(12) United States Patent
Chang et al.

(10) Patent No.: US 11,534,535 B2
(45) Date of Patent: Dec. 27, 2022

(54) BREAST PUMP CONTAINERS AND METHODS

(71) Applicant: WILLOW INNOVATIONS, INC., Mountain View, CA (US)

(72) Inventors: John Chang, Los Altos, CA (US); Brian Mason, Menlo Park, CA (US); Fred Co, Santa Clara, CA (US); Erica Keenan, Menlo Park, CA (US)

(73) Assignee: Willow Innovations, Inc., Mountain View, CA (US)

( * ) Notice: Subject to any disclaimer, the term of this patent is extended or adjusted under 35 U.S.C. 154(b) by 1178 days.

(21) Appl. No.: 16/056,738

(22) Filed: Aug. 7, 2018

(65) Prior Publication Data

US 2018/0339089 A1   Nov. 29, 2018

Related U.S. Application Data

(63) Continuation of application No. PCT/US2017/017212, filed on Feb. 9, 2017.

(60) Provisional application No. 62/293,485, filed on Feb. 10, 2016.

(51) Int. Cl.
*A61M 1/06* (2006.01)
*A61M 39/24* (2006.01)
*A61M 39/22* (2006.01)

(52) U.S. Cl.
CPC ............. *A61M 1/066* (2014.02); *A61M 1/06* (2013.01); *A61M 1/062* (2014.02); *A61M 39/22* (2013.01); *A61M 39/24* (2013.01); *A61M 2205/3331* (2013.01); *A61M 2205/50* (2013.01); *A61M 2209/06* (2013.01)

(58) Field of Classification Search
CPC ...... A61M 1/062; A61M 1/064; A61M 1/067; A61M 1/066; A45F 3/20; B65D 3/26
See application file for complete search history.

(56) References Cited

U.S. PATENT DOCUMENTS

| | | |
|---|---|---|
| 1,197,011 A | 9/1916 | Cilino |
| 4,263,912 A | 4/1981 | Adams |
| 4,311,141 A | 1/1982 | Diamond |
| 4,768,547 A | 9/1988 | Danby et al. |
| 4,821,580 A | 4/1989 | Jorritsma |
| 5,542,921 A | 8/1996 | Meyers et al. |
| 5,634,468 A | 6/1997 | Platt et al. |
| 5,658,133 A | 8/1997 | Anderson et al. |

(Continued)

FOREIGN PATENT DOCUMENTS

| | | |
|---|---|---|
| CN | 2628060 Y | 7/2004 |
| CN | 201692384 | 1/2011 |

(Continued)

OTHER PUBLICATIONS

Chiu et a., Development of a piezoelectric polyvinylldene fluoride (PVDF) polymer based sensor patch for simultaneous heartbeat and respiration monitoring, Sensors and Actuators A: Physical, vol. 189, Jan. 15, 2013, pp. 328-334.

(Continued)

*Primary Examiner* — Nathan R Price
*Assistant Examiner* — Melissa A Snyder

(57) ABSTRACT

Systems and methods for pumping milk from a breast, wherein the milk is expressed from the breast under suction and milk is expulsed from the pumping mechanism to a collection container assembly.

15 Claims, 14 Drawing Sheets

(56) References Cited

U.S. PATENT DOCUMENTS

| | | | |
|---|---|---|---|
| 5,810,772 A | 9/1998 | Niederberger | |
| 5,827,191 A | 10/1998 | Rosenfeld | |
| 6,039,182 A * | 3/2000 | Light | B65D 81/2023 |
| | | | 206/524.8 |
| 6,273,868 B1 | 8/2001 | Nordvik | |
| 6,287,252 B1 | 9/2001 | Lugo | |
| 6,328,082 B1 | 12/2001 | Lafond | |
| D459,233 S | 6/2002 | Young | |
| 6,440,100 B1 | 8/2002 | Prentiss | |
| 6,547,756 B1 | 4/2003 | Greter et al. | |
| 6,579,258 B1 | 6/2003 | Atkin et al. | |
| 6,712,785 B2 | 3/2004 | Morton et al. | |
| 6,840,918 B1 | 1/2005 | Britto et al. | |
| 7,201,735 B2 | 4/2007 | Atkin et al. | |
| 7,223,255 B2 | 5/2007 | Myers et al. | |
| 7,413,557 B2 * | 8/2008 | Samson | A61M 1/82 |
| | | | 604/74 |
| 7,621,797 B1 | 11/2009 | Hershkovich | |
| 7,661,534 B2 | 2/2010 | Saclier et al. | |
| 7,824,363 B2 | 11/2010 | Myers | |
| 7,972,297 B2 | 7/2011 | Bryan et al. | |
| 7,988,661 B2 | 8/2011 | Silver et al. | |
| 8,057,425 B1 * | 11/2011 | Myers | A61M 1/062 |
| | | | 604/74 |
| 8,070,715 B2 | 12/2011 | Quackenbush et al. | |
| 8,070,716 B2 | 12/2011 | Sutrina et al. | |
| 8,262,606 B2 | 9/2012 | Greter et al. | |
| 8,282,596 B2 | 10/2012 | Greter et al. | |
| 8,353,865 B2 | 1/2013 | Thilwind et al. | |
| 8,357,116 B2 | 1/2013 | Simdon | |
| 8,376,986 B2 | 2/2013 | Van Schijndel et al. | |
| 8,449,520 B2 | 5/2013 | Pepper et al. | |
| 8,671,701 B2 | 3/2014 | McKendry | |
| 8,684,961 B2 | 4/2014 | Gottenbos et al. | |
| 8,801,495 B1 | 8/2014 | Guindon | |
| 9,050,404 B2 | 6/2015 | Silver et al. | |
| 9,162,016 B2 | 10/2015 | Geddes | |
| 9,173,587 B2 | 11/2015 | Van Schijndel et al. | |
| 9,199,017 B2 | 12/2015 | Greter | |
| 9,278,167 B2 | 3/2016 | Aalders et al. | |
| 9,452,857 B2 | 9/2016 | Corbett et al. | |
| 9,616,156 B2 | 4/2017 | Alvarez et al. | |
| 9,683,562 B2 | 6/2017 | Davis et al. | |
| 9,878,078 B1 * | 1/2018 | Levine | A61M 1/062 |
| 10,434,230 B2 * | 10/2019 | Rigert | A61M 1/06 |
| 2003/0191433 A1 | 10/2003 | Prentiss | |
| 2004/0024351 A1 | 2/2004 | Greter et al. | |
| 2004/0101414 A1 | 5/2004 | Gharib et al. | |
| 2004/0127845 A1 | 7/2004 | Renz et al. | |
| 2005/0059928 A1 | 3/2005 | Larsson | |
| 2005/0234370 A1 | 10/2005 | Beal et al. | |
| 2006/0106334 A1 | 5/2006 | Jordan et al. | |
| 2008/0177224 A1 * | 7/2008 | Kelly | A61M 1/06 |
| | | | 604/74 |
| 2008/0208116 A1 * | 8/2008 | Dao | A61M 1/064 |
| | | | 604/74 |
| 2008/0243059 A1 | 10/2008 | Yamashita et al. | |
| 2009/0024080 A1 | 1/2009 | Rohrig | |
| 2010/0102085 A1 | 4/2010 | Kanfer et al. | |
| 2010/0106082 A1 | 4/2010 | Zhou | |
| 2010/0217148 A1 | 8/2010 | Binder | |
| 2011/0071466 A1 | 3/2011 | Silver et al. | |
| 2011/0196291 A1 | 8/2011 | Vischer et al. | |
| 2011/0245763 A1 | 10/2011 | Myers | |
| 2011/0270162 A1 | 11/2011 | Guo | |
| 2012/0101575 A1 | 4/2012 | Horne et al. | |
| 2012/0165729 A1 | 6/2012 | Cudworth | |
| 2012/0277636 A1 | 11/2012 | Blondheim et al. | |
| 2012/0277728 A1 | 11/2012 | Weber et al. | |
| 2013/0023821 A1 | 1/2013 | Khalil et al. | |
| 2013/0123688 A1 | 5/2013 | Bosman et al. | |
| 2013/0131588 A1 | 5/2013 | Silver et al. | |
| 2014/0066734 A1 | 3/2014 | Zdeblick | |
| 2014/0378895 A1 | 12/2014 | Barack | |
| 2014/0378946 A1 | 12/2014 | Thompson et al. | |
| 2015/0065994 A1 | 3/2015 | Fridman et al. | |
| 2015/0100016 A1 | 4/2015 | Liao | |
| 2015/0148709 A1 | 5/2015 | Mardiks et al. | |
| 2015/0196247 A1 | 7/2015 | Lau | |
| 2016/0000980 A1 | 1/2016 | Alvarez et al. | |
| 2016/0014494 A1 | 1/2016 | Krissman et al. | |
| 2016/0015876 A1 | 1/2016 | Tattersfield et al. | |
| 2016/0256618 A1 | 9/2016 | Embleton | |
| 2016/0287769 A1 | 10/2016 | Makower et al. | |
| 2017/0072118 A1 | 3/2017 | Makower et al. | |
| 2017/0080134 A1 | 3/2017 | Makower et al. | |
| 2017/0173232 A1 | 6/2017 | Chang et al. | |

FOREIGN PATENT DOCUMENTS

| | | |
|---|---|---|
| EP | 2456482 B1 | 11/2016 |
| EP | 3151876 B1 | 11/2017 |
| GB | 2342446 A | 4/2000 |
| JP | H5-330564 A | 12/1993 |
| JP | 2005279044 | 10/2005 |
| RU | 2012 107356 | 5/2012 |
| WO | WO1996022116 | 7/1996 |
| WO | WO 2000/57934 | 10/2000 |
| WO | WO2001054488 | 8/2001 |
| WO | WO2011010255 | 1/2011 |
| WO | WO2011144984 A | 11/2011 |
| WO | WO2012037848 | 3/2012 |
| WO | WO 2013076055 | 5/2013 |
| WO | WO2013088310 | 6/2013 |
| WO | WO 2013/187763 | 12/2013 |
| WO | WO2013184004 | 12/2013 |
| WO | WO2015120321 | 8/2015 |

OTHER PUBLICATIONS

Double Electric Breast Pump/Dr. Brown's, http://www.drbrownsbaby.com/breastfeeding-product/breast-pumps/double-electric, May 15, 2014.

The Revolutionary New Freemie Collection Cups, User Manual, Mar. 17, 2015.

* cited by examiner

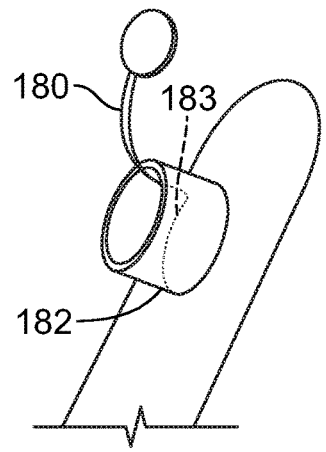
FIG. 19
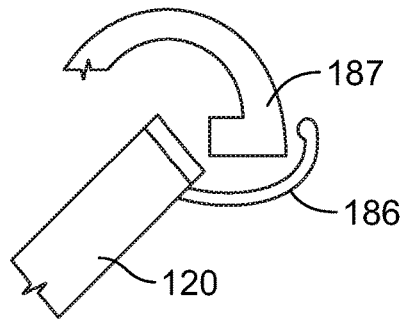
FIG. 20
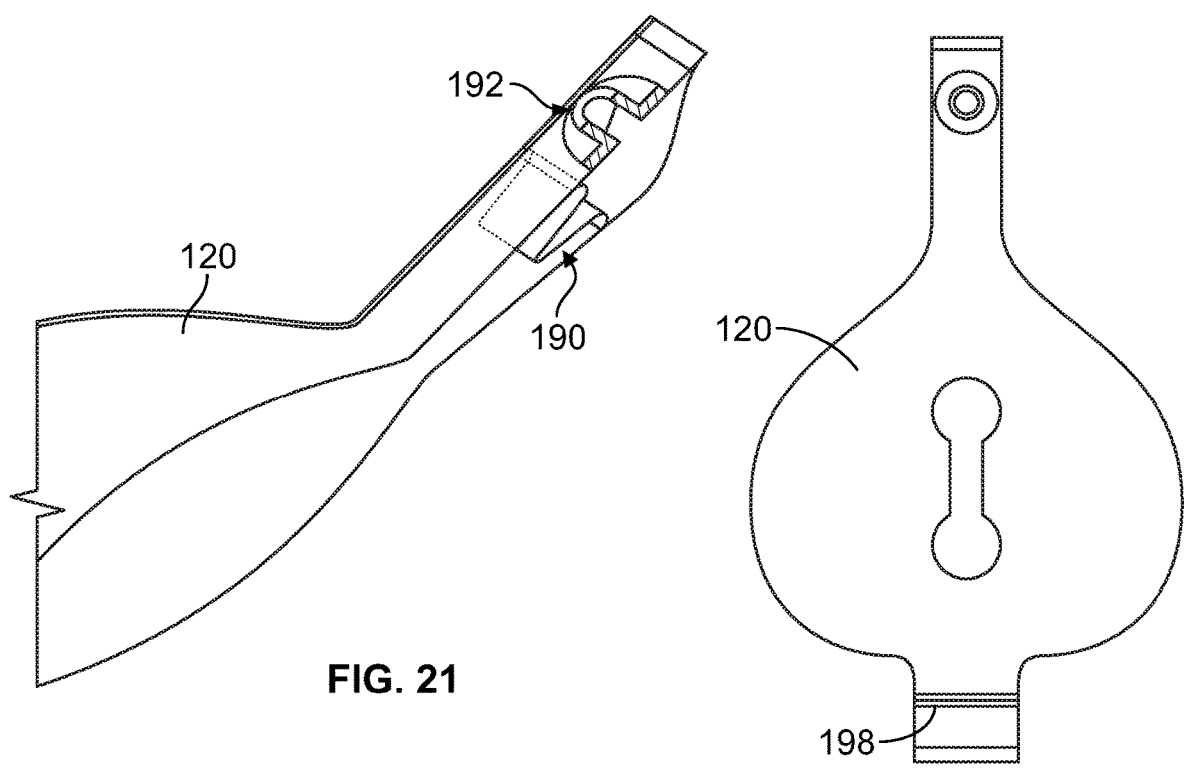
FIG. 21
FIG. 22

BREAST PUMP CONTAINERS AND METHODS

FIELD OF THE DISCLOSURE

The present disclosure generally relates to container assemblies for portable breast pump systems and methods for collecting milk from a breast of a nursing mother.

BACKGROUND OF THE DISCLOSURE

As more women become aware that breastfeeding is the best source of nutrition for a baby, and also offers health benefits to the nursing mother, the need is increasing for breast pump solutions that are user-friendly, quiet, discrete and versatile for use by a nursing mother in various situations. This is particularly true for the working mother, who is away from the home for eight to ten hours or more and needs to pump breast milk in order to have it available for her baby, but it is also a requirement for many other situations where the mother is away from the privacy of the home for an extended period, such as during shopping, going out to dinner or other activities.

Although a variety of breast pumps are available, a number are awkward and cumbersome, requiring many parts and assemblies and being difficult to transport. Hand pump varieties that are manually driven are onerous to use and can be inconvenient to use. Some powered breast pumps require an AC power source to plug into during use. Some systems are battery driven, but draw down the battery power fairly rapidly as the motorized pump continuously operates to maintain suction during the milk extraction process. Certain other of the breast pumps available are lacking in convenient storage containers. The storage containers can be difficult to package, install, remove and store thereby creating a barrier to effective use.

There is thus a continuing need for conveniently usable and effective container assemblies for portable wearable breast pump. The present disclosure addresses these and other needs.

SUMMARY OF THE DISCLOSURE

Briefly and in general terms, the present disclosure is directed toward container assemblies for a breast pump system. The system includes breast contacting structure and a storage container, and structure that delivers milk or other liquid from a breast to the storage container. The method involves pumping milk from a breast and delivering the pumped milk into the container assembly.

According to one aspect of the present disclosure, a system for pumping milk from a breast includes a container assembly in combination with one or more of: a skin contact member or flange configured to form a seal with the breast; a conduit in fluid communication with and connected to the skin contact member; a driving mechanism configured to establish a vacuum profile within the conduit; an external shell; and a non-transitory computer readable medium having stored thereon instructions executable by a computing device to cause the computing devices to perform functions associated with and directed by the firmware; wherein the external shell comprises a compartment facing a distal end of the external shell, the external shell further comprising a proximal end surface facing away from the proximal end; wherein the skin contact member, the conduit and the driving mechanism are received in the compartment of the external shell; wherein the milk collection container is positionable within the shell; and wherein the system is shaped and configured to be contoured to the breast of a user.

In various embodiments, the storage container can be specifically configured to prevent kinking and for durability and handling. A flow feature can be incorporated into the storage container, valves and materials can be chosen to facilitate removing air or gases, tabs and wings can be provided for handling, and structure adapted for the removal of milk from a container assembly. The container can be pre-formed to optimize or maximize space within a pump system. Further, the container can be placed into a flattened configuration to facilitate effective packaging.

In at least one embodiment, the flange or skin contact member, the conduit, the driving mechanism, the external shell and the milk collection container are all contained within a cup of a brassiere.

In at least one embodiment, the milk collection container comprises a one-way valve that permits milk inflow into the milk collection container but prevents milk backflow from the milk collection container to the conduit.

In at least one embodiment, the system further includes a milk collection container, wherein the milk collection container is in fluid communication with the conduit.

According to another aspect of the present disclosure, a method of operating a system for pumping milk into a storage container includes one or more of: providing the system comprising a skin contact member configured to form a seal with the breast, a conduit in fluid communication with and connected to the skin contact member; a driving mechanism including a compression member configured to compress and allow decompression of the conduit in response to inward and outward movements of the compression member, a sensor, and a controller configured to control operation of the driving mechanism; sealing the skin contact member to the breast; operating the driving mechanism to generate predetermined pressure cycles within the conduit; monitoring by the controller of at least one of position and speed of movement of the compression member relative to the conduit; measuring or calculating pressure within the conduit; maintaining or modifying motion of the compression member as needed, based upon feedback from the calculated pressure and at least one of position and speed of movement of the compression member, to ensure that the predetermined pressure cycles continue to be generated.

These and other features of the disclosure will become apparent to those persons skilled in the art upon reading the details of the systems and methods as more fully described below.

BRIEF DESCRIPTION OF THE DRAWINGS

FIG. 19 shows another approach to a valve.

FIG. 20 shows still yet another approach to a valve arrangement.

FIG. 21 is a cutaway view, showing a further approach to a container assembly.

FIG. 22 shows yet another further approach to a container assembly with pouring structure.

DETAILED DESCRIPTION OF THE DISCLOSURE

Before the present systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a sensor" includes a plurality of such sensors and reference to "the pump" includes reference to one or more pumps and equivalents thereof known to those skilled in the art, and so forth.

The publications discussed herein are provided solely for their disclosure prior to the filing date of the present application. The dates of publication provided may be different from the actual publication dates which may need to be independently confirmed.

Figure 1A:
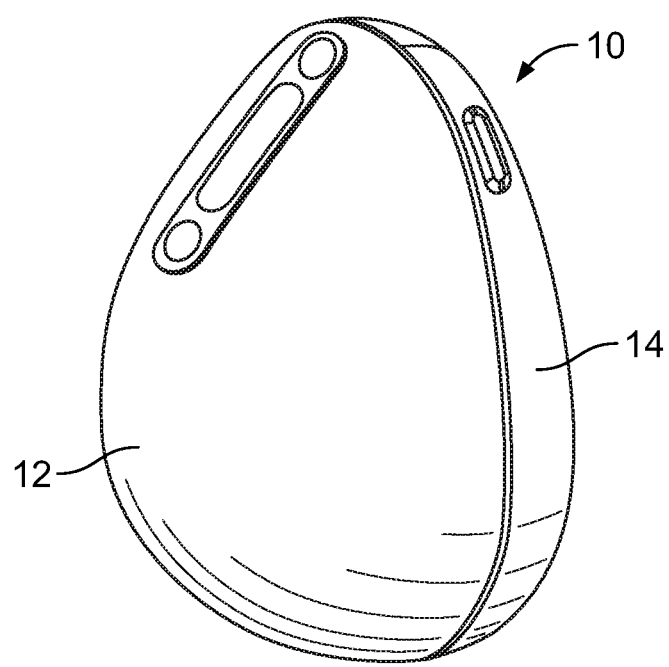
FIG. 1A shows a perspective view of a breast pump system according to an embodiment of the present disclosure.
Figure 1B:
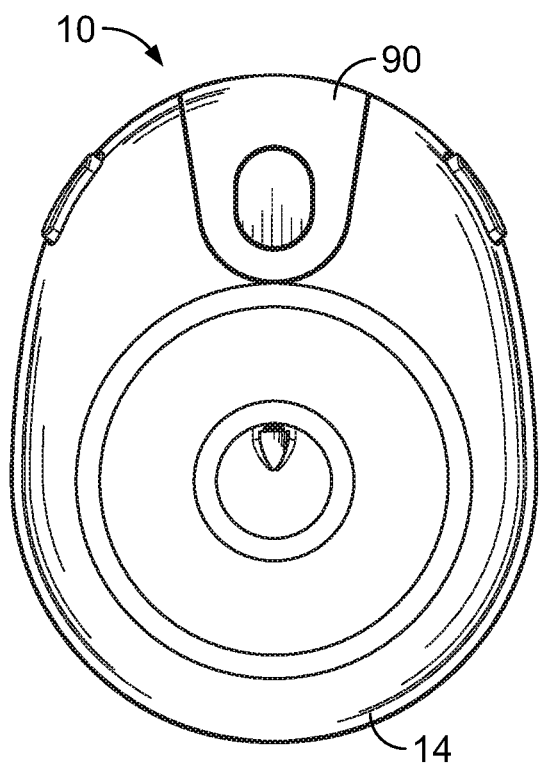
FIG. 1B shows a rear view of the system of FIG. 1.

Various details of the present system can be found in PCT Application Nos. PCT/US15/41257, PCT/US15/41271, PCT/US15/41277, and PCT/US15/41285 each filed Jul. 21, 2015, and PCT/US15/50340 filed Sep. 16, 2015, each of which are hereby incorporated herein, in their entireties, by reference thereto FIGS. 1A-B are perspective and back views of a breast pump system 10 according to an embodiment of the present disclosure. The breast pump system 10 can include one or more of the below introduced or described features or functions, or a combination thereof. The housing or outer shell 12 of system 10 can be shaped and configured to be contoured to the breast of a user and to thus provide a more natural appearance when under the clothing of the user. As can be appreciated from the figures, the system can define a natural breast profile. The natural breast profile is contemplated to fit comfortably and conveniently into a bra of a user and to present a natural look. As such, the profile is characterized by having a non-circular base unlike that embodied in a generally dome-shaped configuration. Extending from the base are curved surfaces having asymmetric patterns. Moreover, like natural breasts, the profile of the device or system is contemplated to define one or more asymmetric curves and off-center inertial centers. Various natural breast shapes can be provided to choose from to the tastes and needs of a user. An opposite side of the pump system 10 is configured with a flange 14 which is sized and shaped to engage a breast of a user. The flange 14 is contoured to comfortably fit against a wide range of user's bodies and to provide structure for sealingly engaging with breast tissue.

Figure 2:
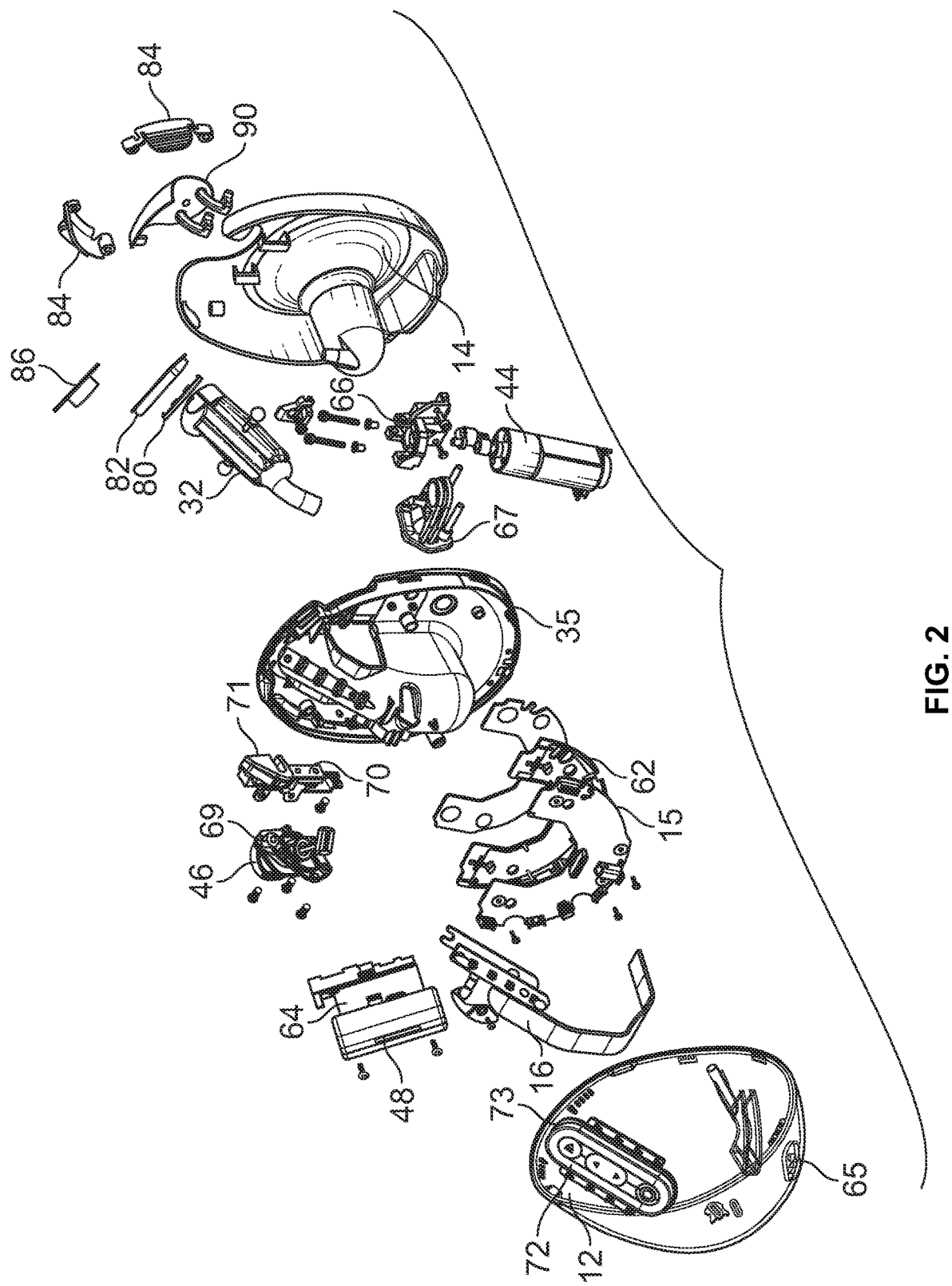
FIG. 2 is an exploded view of the system of FIG. 1, depicting mechanical components of the system.

FIG. 2 depicts an exploded view of structural and mechanical components of the system 10. A housing overmold 61 shaped and sized to overlay the housing 12 is provided and can include a pattern of swirling lines that define a pleasing ornamental appearance to the system 10. Configured between the housing 12 and flange 14 is the chassis 35. Notably, the chassis can be configured to snap into engagement with the housing 12. Moreover, in a preferred embodiment, the chassis 35 supports directly or indirectly all of the pump components. In particular, a PCB controller mount 63 is supported by the chassis 35 and is configured to be connected to and support a circuit board (not shown). A battery bracket 64 is also supported by the chassis 35 and is sized and shaped to receive a rechargeable battery assembly that powers the system 10. A cover jack 65 is further included to provide access to the battery assembly and for accepting a power cord connector (not shown). Motor mounting 66 and motor receiver structure 67 is also supported by the chassis 35 and are configured to receive and support the system motor which is powered by the battery and which functions to move actuators operating on the flex conduit or tube 32. Also supported by the chassis 35 are an actuator bracket 69, and a load cell bracket 70 and load cell receiver 71. Moreover, user interface panel can include a button membrane 72 and a button membrane housing 73 each supported on the housing 12 that provides the user with system control.

In order to connect the flex conduit or tube assembly 32 to the system 10, there are provided a flex conduit or tube ring 80 and a flex conduit or tube collar 82. The flex conduit or tube collar 82 is sized and shaped to be received into a pair of spaced snap buttons 84. In one specific embodiment, a fluid container fitment 86 (shown in isolation from the container) can be sized and shaped to be received into the flex conduit or tube collar 82. A door assembly 90 is attached to the flange 14 and configured to swing open and closed to both provide access to an interior of the system 10 as well as to support a robust connection between the fitment 86 and flex conduit or tube collar 82 as described in more detail below.

Figure 3:
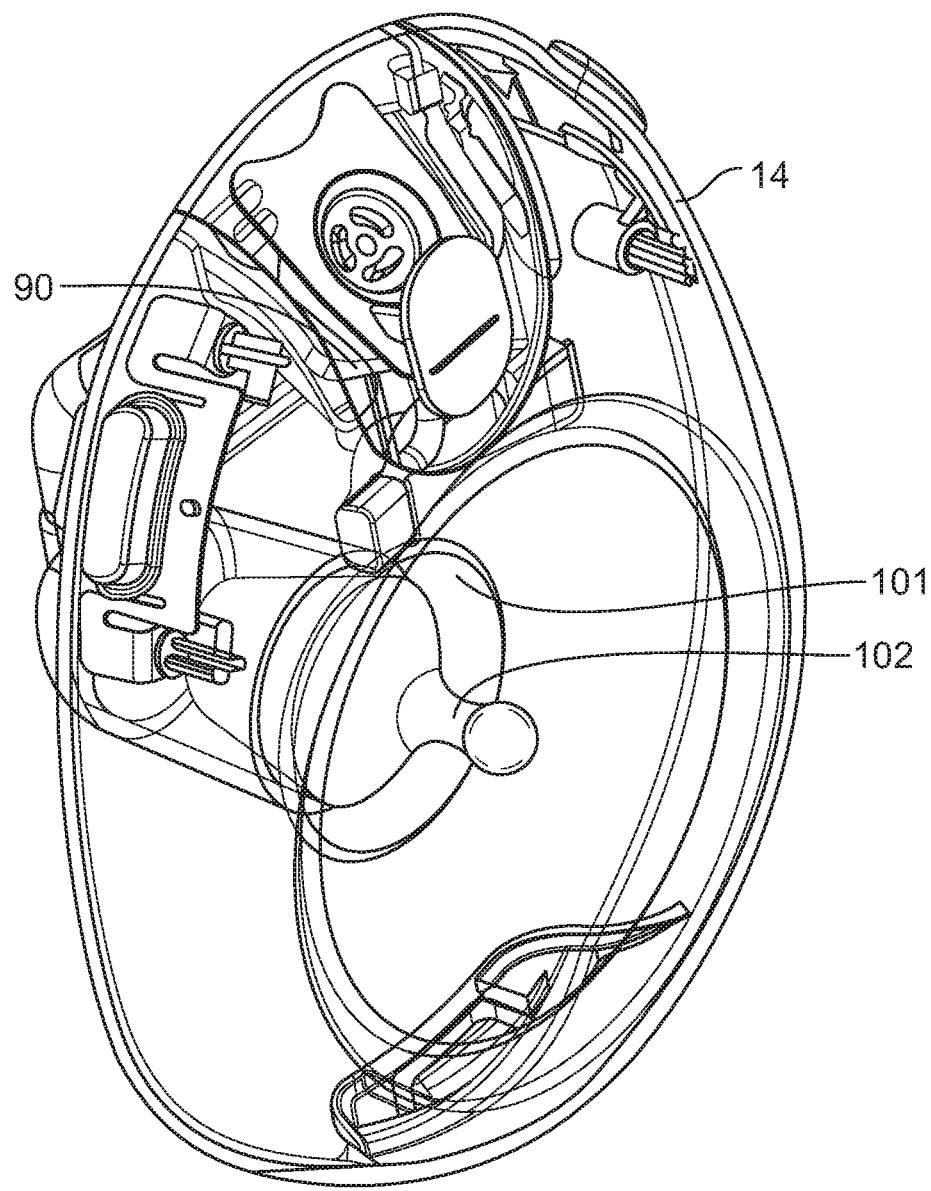
FIG. 3 is a perspective view, depicting an approach to sealing the flange assembly.
Figure 4:
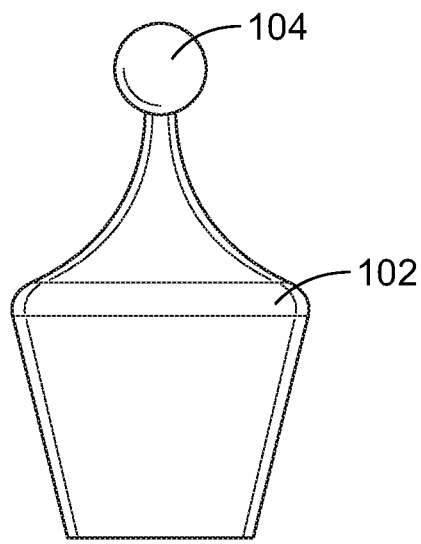
FIG. 4 is an enlarged view, depicting a plug of the sealing approach of FIG. 3.

As shown in FIG. 3 where the flange 14 is shown as transparent, the system 10 can include additional structure to prohibit residual milk from spilling out from the flange 14 after completion of a pumping session or during a break in pumping. The flex conduit or tube 32 and flange 14 can retain residual milk that might spill when removing the pump system 10 from the breast or when the pump system is placed in a purse or elsewhere for temporary storage. That is, residual milk can spill out of the nipple receiving portion 101 of the flange 14. A plug 102 (See also FIG. 4) can be sized and shaped to be sealingly retained within the nipple receiving portion 101 to prohibit residual milk from exiting the system 10 through the flange 14. The plug 102 can include a handle 104 assuming various shapes such as a ball tip for grasping, and a body that is tapered and defines a generally circular shape in cross-section. In this way, the plug 102 can both sealingly engage with the nipple receiving portion 101 as well as be conveniently handled.

Figure 5:
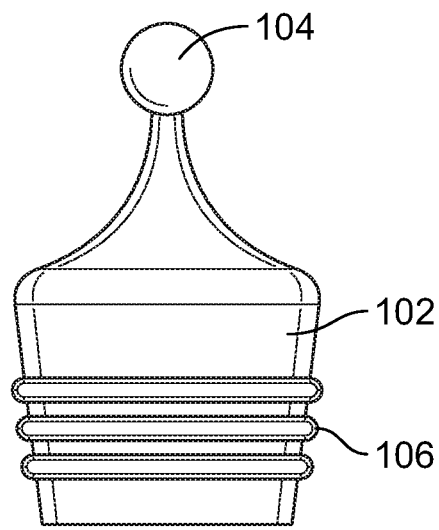
FIG. 5 is an enlarged view, depicting another approach to a plug.
Figure 6:
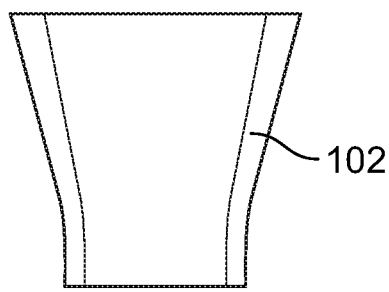
FIG. 6 is an enlarged view, depicting yet another approach to a plug.
Figure 7:
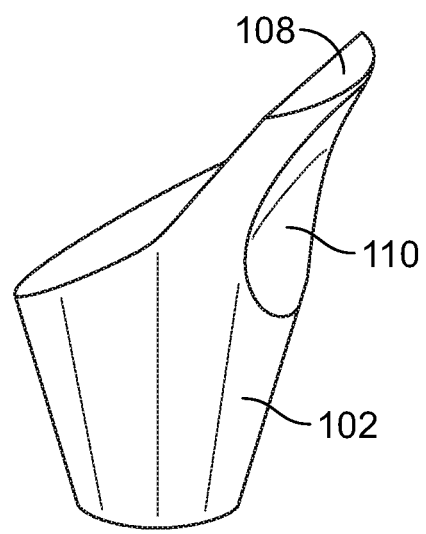
FIG. 7 is an enlarged view, depicting still yet another approach to a plug.

In alternative approaches to the plug 102, there can also be included one or more annular rings 106 configured about the body of the plug to facilitate sealing of the plug 102 with the nipple receiving portion 101 of the flange 14 (FIG. 5). The plug 102 can also lack the handle portion (FIG. 6) and have a body shaped like a cork, or include a tapering handle 108 with an asymmetric thumb receiving indent 110 for grasping (FIG. 7).

As described in connection with the embodiments presented below, the system 10 can be configured to pump into a sealed container assembly, or one that includes an integral valve or an otherwise airtight container assembly, or combinations thereof. In one or more approaches, the valve can be integrally formed with a bag assembly such that it is molded along with one or more sheets defining bag structure. Sealed and/or airtight containers can hold liquids and gases without permitting a leak. Gas or liquids can be removed from such containers through a valve that is configured to be opened or defeated temporarily or permanently. Alternatively, an opening separate from the valve can be provided in the container, or the container can be configured to be split open or include scoring to aid in opening the container. Moreover, there are contemplated a range of disposable and durable combinations of container and valve fitment arrangements such that one or both of the container bag and fitment are disposable or reusable. Further, the container assembly has features to avoid failures such as the fitment rubbing through container bag film during vibrations associated with transport or use. The assembly can also have features so that the container bag and fitment are not damaged during loading or unloading and while in storage. Moreover, in at least one embodiment, the milk collection container can comprise a one-way valve that permits milk inflow into the milk collection container but prevents milk backflow from the milk collection container to the conduit. In one embodiment, the collection container or container assembly includes an extra part, valve or fitment that is attached thereto and facilitates creating a seal with the container to establish a closed system. In one embodiment, the milk container can include a one-way valve that cannot be removed without destroying milk container or valve function. The valve can assume a myriad of shapes and kinds including an umbrella valve, a duckbill valve, a ball valve or other valve. Moreover, in one or more embodiments, the container can be flexible or rigid, or disposable or reusable.

Figure 8:
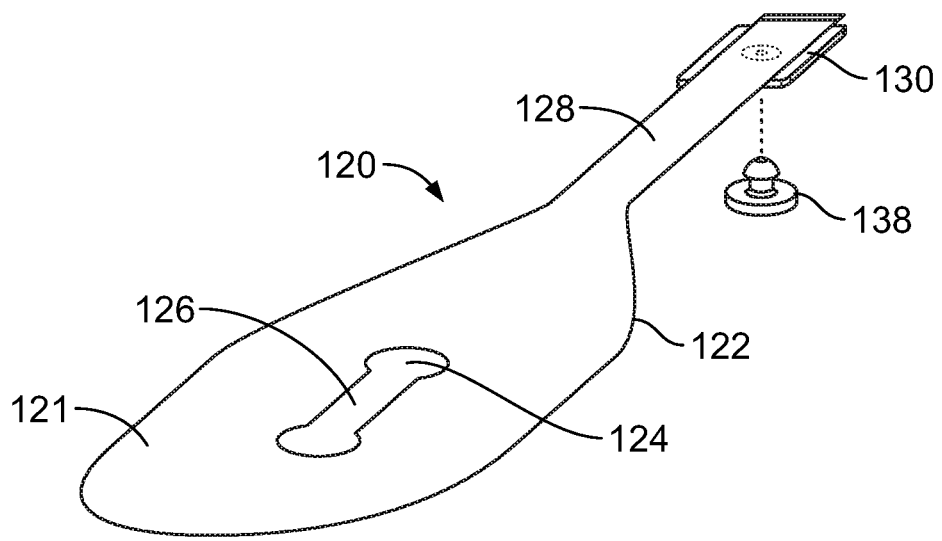
FIGS. 8-10 show one approach to a container assembly arrangement.
Figure 9:
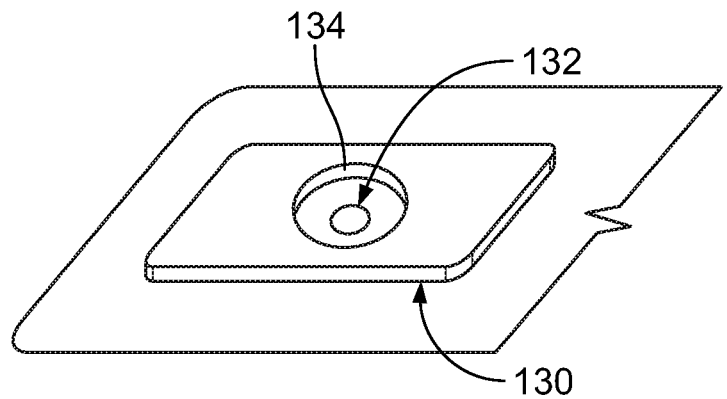
Figure 10:
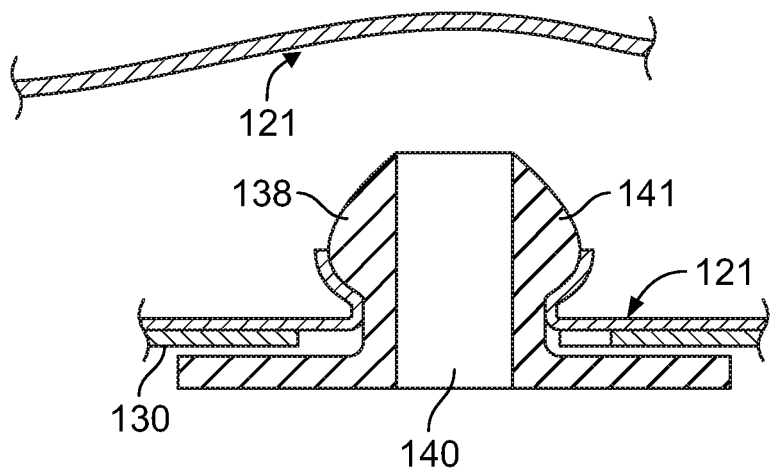
Figure 11A:
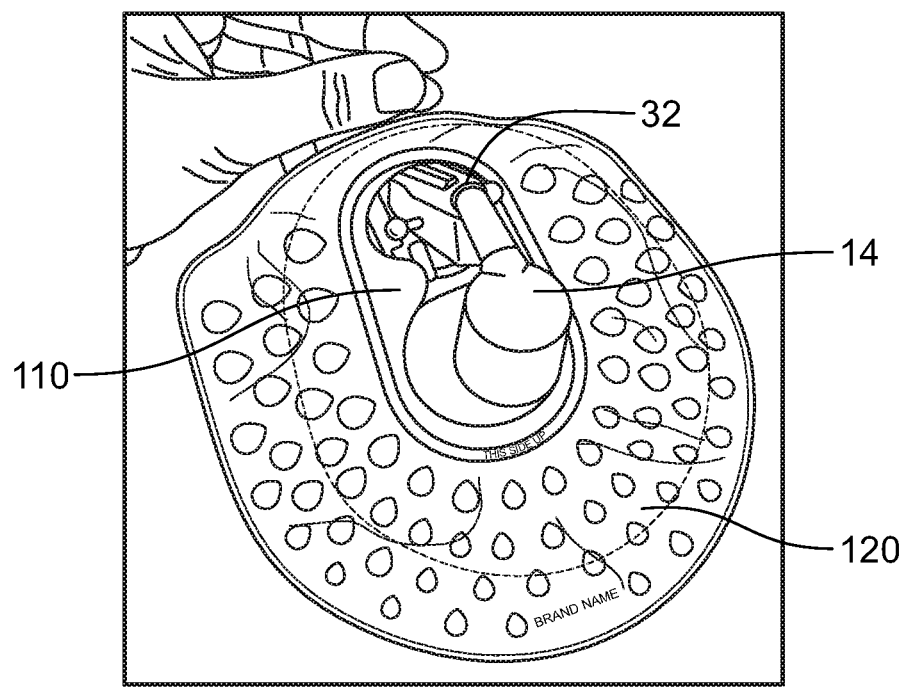
FIGS. 11A-D show various steps involved in installing a container assembly.
Figure 11B:
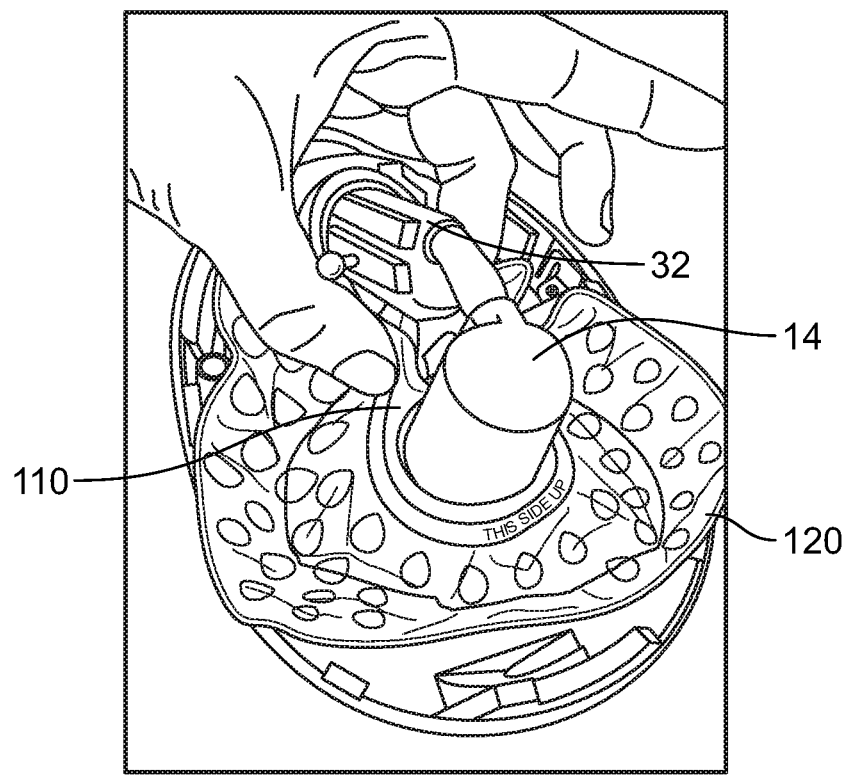
Figure 11C:
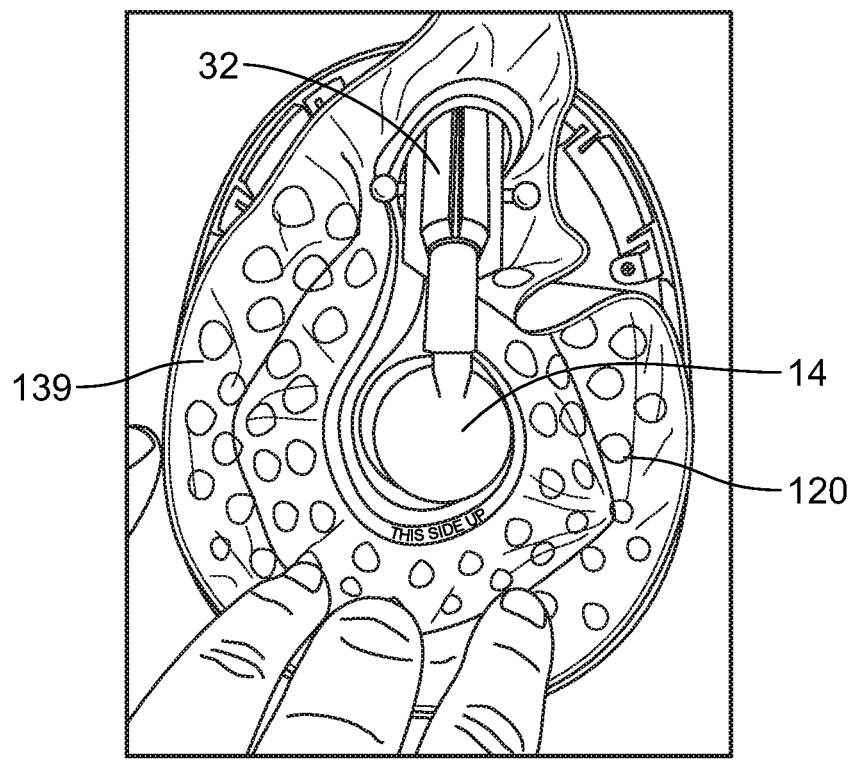
Figure 11D:
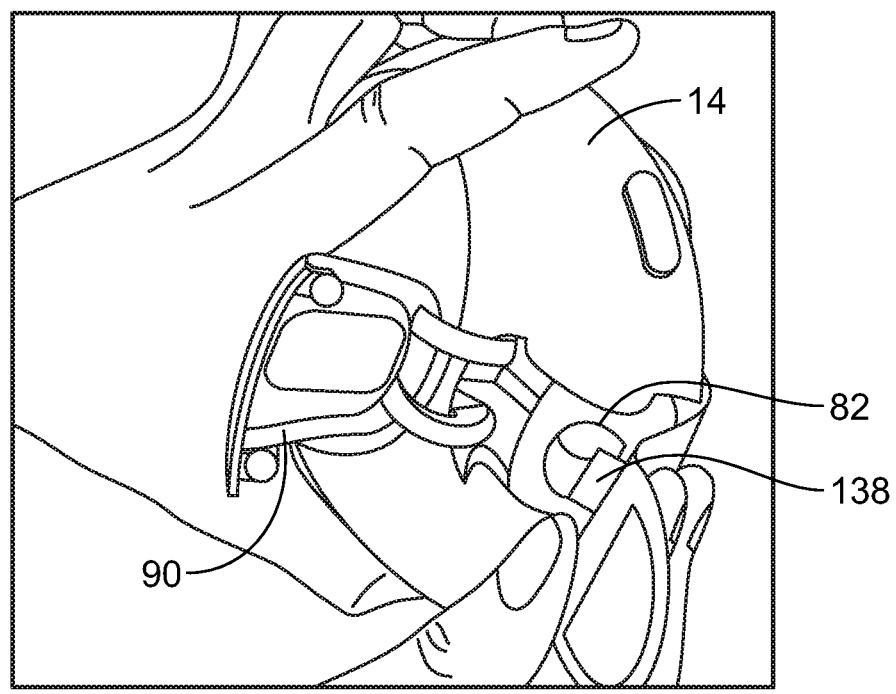

Turning now to FIGS. 8-10, one embodiment of a sealed or sealable container assembly 120 is shown. In one particular embodiment, the container assembly 120 can be formed from about two 2.5-3.0 mil sheets 121 of material that is joined (i.e., welded) together along a perimeter 122 of the assembly, and can be sized to retain up to 4.5 ounces, or alternatively 8 ounces of fluid. A body of the container assembly is shaped to fit within flange 14 and includes a generally asymmetrical central opening 124 created by an interior seal. Material 126 extends into the central opening 124 to define a pair of spaced curved flaps and are provided for handling and facilitating positioning of the container assembly 120 within a pump system 10. A narrow neck portion 128 is centrally positioned and extends longitudinally away from the central opening 124. The container assembly 120 can be re-sealable, re-usable, include larger or smaller openings, or include spout structure for pouring contents. Thus, in alternative embodiments, the container assembly 120 can be re-sealable, re-usable, include larger or smaller openings or include spout structure for pouring contents. The valve of the container assembly can also be re-usable with a second or subsequent container assembly, and therefore is removable from the container assembly.

Moreover, in one particular embodiment, the container assembly 120 can be made from polyethylene and can be bisphenol A free, as well as food grade material. It is freezable without tearing and withstand approximately 0-80 degree Celsius temperatures. Additionally, tensile strength can be from 2300-2900 psi and tear strength from 440-600 psi, with a water vapor transmission rate max of about 0.5 g/100 in2/24 hrs and an oxygen transfer rate of about 150 cc/100 in2/24 hrs. In alternate embodiments, the material of the container assembly can be Gore-tex or Tyvek, for example. Such alternative materials can permit out-gasing such that any air that is pumped into the container assembly will escape through the material while the container assembly retains the fluid. In this specific regard, other vents or approaches to venting the system can be incorporated into one or more embodiments. Thus, self-venting of the container assembly or active venting while using the pump system or after use can be accommodated. In one approach, a pressure valve can be incorporated into the system and configured to activate after some system pressure is reached, and further the valve can be designed to act as a fluid barrier, only allowing air and not fluid to escape. The container assembly can also additionally or alternatively include a rigid or flexible sealing component, such as a ring or gasket into which the pump or container valve is pushed or twisted and sealed.

The container assembly 120 can further include a relatively stiff grommet 130 adhered to the material forming the container assembly. A hole 132 can be formed in one layer of the sheet material 121 of the container assembly 120, a central hole 134 formed in the grommet providing access to and supporting the hole 132 which is undersize with respect to the central hole 134. A pump outlet 138 having a through hole 140 and a barbed body 141 can be provided and can be formed from turned Delrin for example. Utilizing plastic deformation of the sheet material 121, a one-time seal can be created by stretching the sheet material 121 over the barbed body 141 creating the completed assembly depicted in cross-section in FIG. 10.

Various steps in loading a container assembly 120 into the system 10 is shown in FIGS. 11A-D. In a first step (FIG. 11A), the flange 14 is removed from engagement with the remainder of the system 10. Attached to the flange is the flex conduit or tube 32. A central portion of the container assembly 120 is placed over a central projection 110 of the flange 14 and the flex conduit or tube 32. Next, the user can pinch the container assembly and configure it under the flex conduit or tube 32 (FIG. 11C) followed by tucking the container 120 into the flange 14. The opening 132 is fluidly connected to the flex conduit or tube 32 such as via the pump outlet 138 (See FIG. 11D). Once connected the door assembly 90 can be rotated over the flex conduit or tube collar 82 and pump outlet connection (See FIG. 1A) to provide support and a robust engagement between the parts. In certain embodiments, the container assembly 120 can have useful labels, icons or notifications. For example, milk droplet icons 139 can be printed on the container 60 in increasing size to indicate the degree to which the container is filled such as when the milk collected is filled to the larger icons, the user will know that the container assembly is filling up. When the level of the milk corresponds to the smaller icons, then the user will know that the container is less fill. Moreover, a "this side up" message can be included to aid the user in properly installing container 60.

It is contemplated that the door assembly 90 (See FIGS. 1B, 11D) can be employed to both provide a continuous contour of the flange 14 for engaging a user's breast as well as to support the engagement of the container assembly 120 with the system 10. Thus, the door assembly 90 can be configured to pivot with respect to the flange 14, and employed to close the system 10 as it is snapped over and closes the pump. With this approach, the container assembly 120 is securely sandwiched within the door assembly 90. The collar 82 can also provide rigidity to the flex conduit or tube 32 so that it can be loaded into the flange 14 as well as to provide an annular back-up.

In at least one embodiment, the pressure at which a valve between the pump system and the container assembly opens to allow flow into the milk collection container is about 25 mm Hg. The valve can be configured and designed such that it allows fluid to flow through it when the pressure in flex conduit or tubing 32 is positive, e.g., about 25 mm Hg, or some other predesigned "opening pressure". The action of compression elements on the flex conduit or tube 32 cycles between increasing vacuum when the compression elements move in a direction away from flex conduit or tube 32 and decreasing when the compression elements compress the flex conduit or tube 32, but typically should not increase the vacuum to greater than the predetermined maximum vacuum. As the compression elements compress the flex conduit or tube 32, the pressure in the system 10 goes up and reaches the minimum suction level (e.g., latch suction level, such as −60 mmHg, −30 mm Hg, or some other predetermined latch suction level), at which time a compression member (pinch valve) seals off a portion of the flex conduit or tube 32 thereby maintaining the minimum suction (latch suction) against the breast. Continued compression of the flex conduit or tube 32 continues to increase the pressure downstream until the opening pressure is reached (e.g., 25 mm Hg or some other predetermined, positive opening pressure), that opens the valve. The compression elements continue compressing flex conduit or tube 32, pumping fluid (milk) through the valve and into the collection container assembly.

Figure 12:
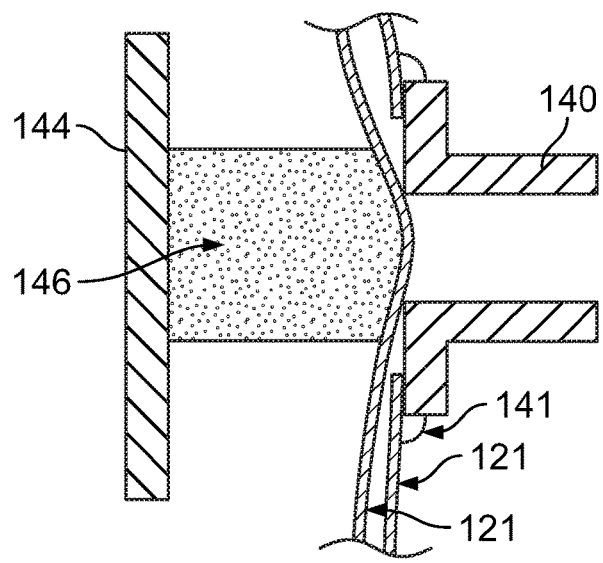
FIGS. 12-14 show an alternative approach to a container assembly arrangement.
Figure 13:
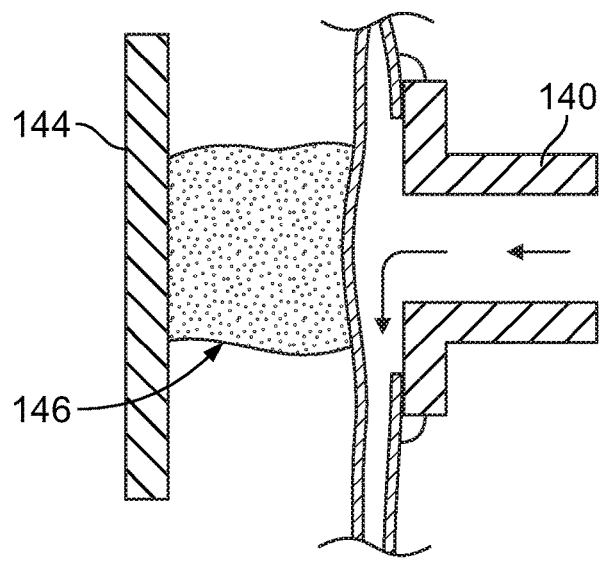
Figure 14:
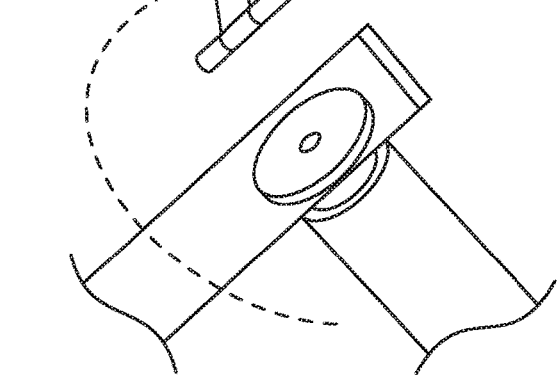
Figure 15:
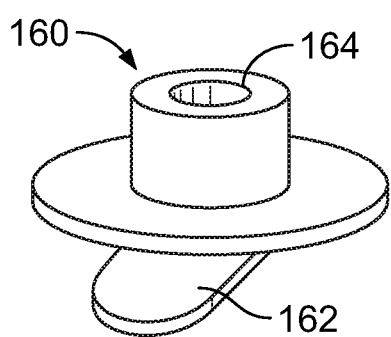
FIGS. 15-16 show another alternative approach to a valve assembly arrangement.
Figure 16:
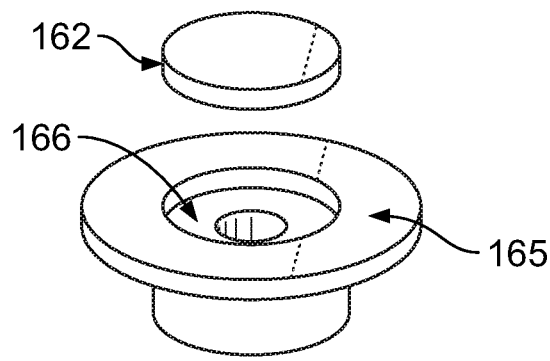
Figure 17:
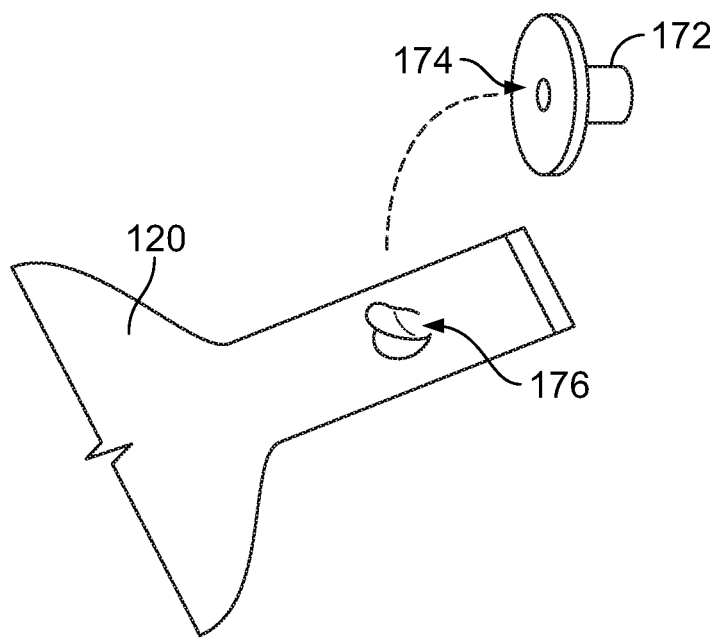
FIGS. 17-18 show a container assembly with yet another approach to a valve arrangement.
Figure 18:
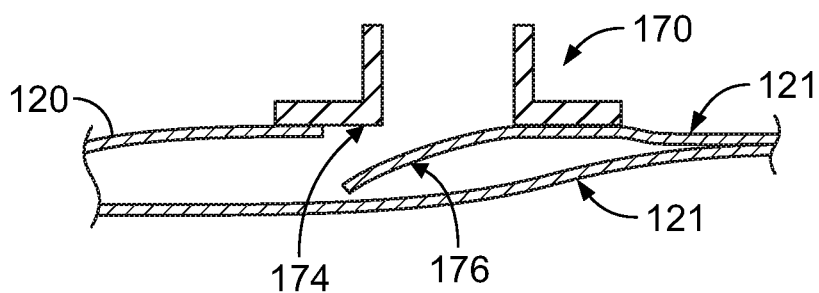
Figure 23:
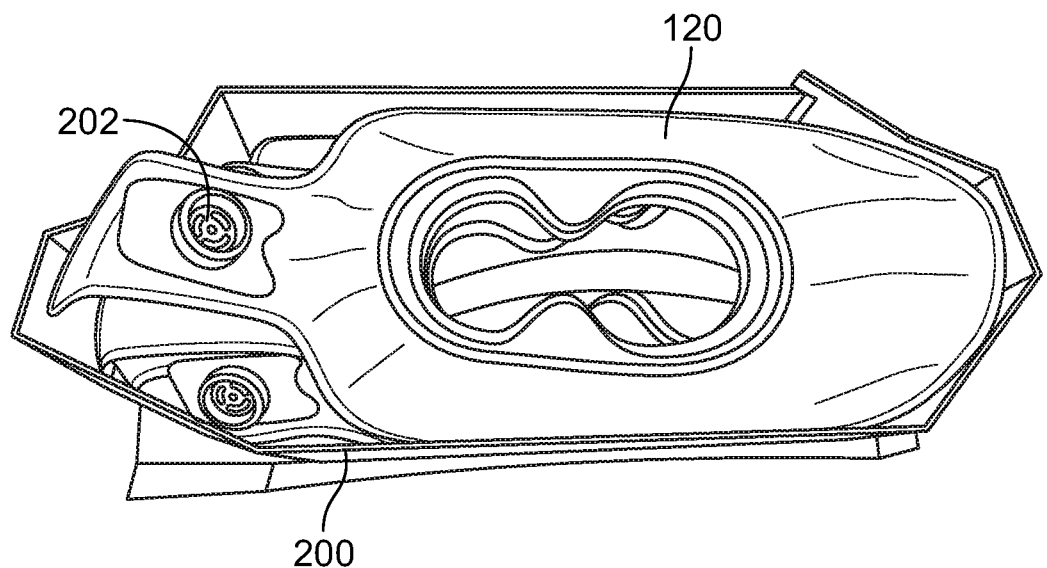
FIG. 23 shows one approach to storing and structure for dispensing a container assembly.
Figure 24:
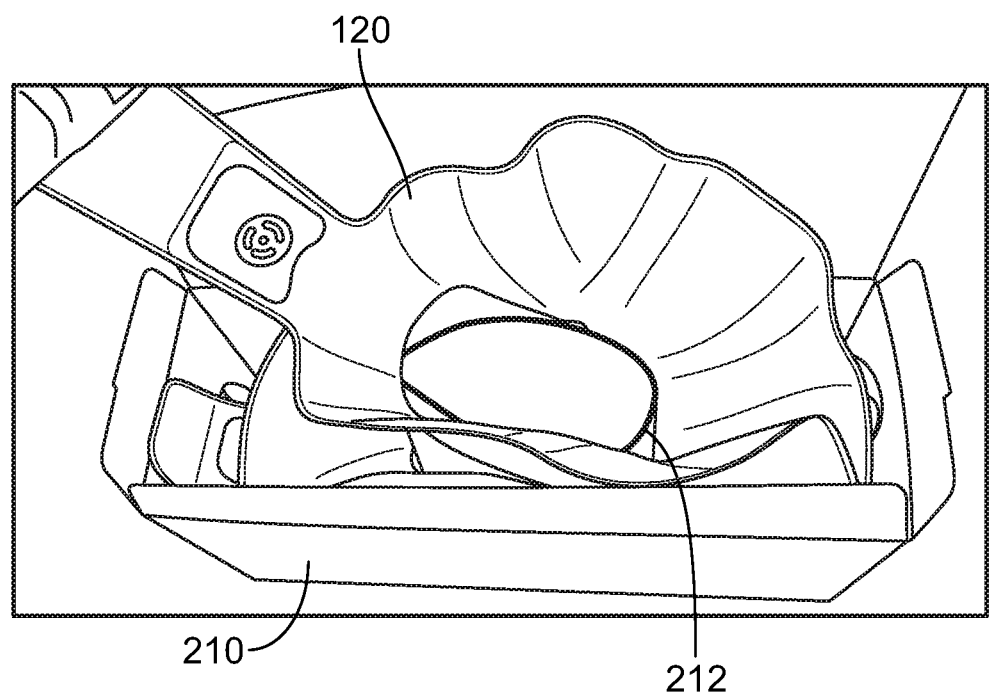
FIG. 24 shows another approach to storing and dispensing a container assembly.
Figure 25:
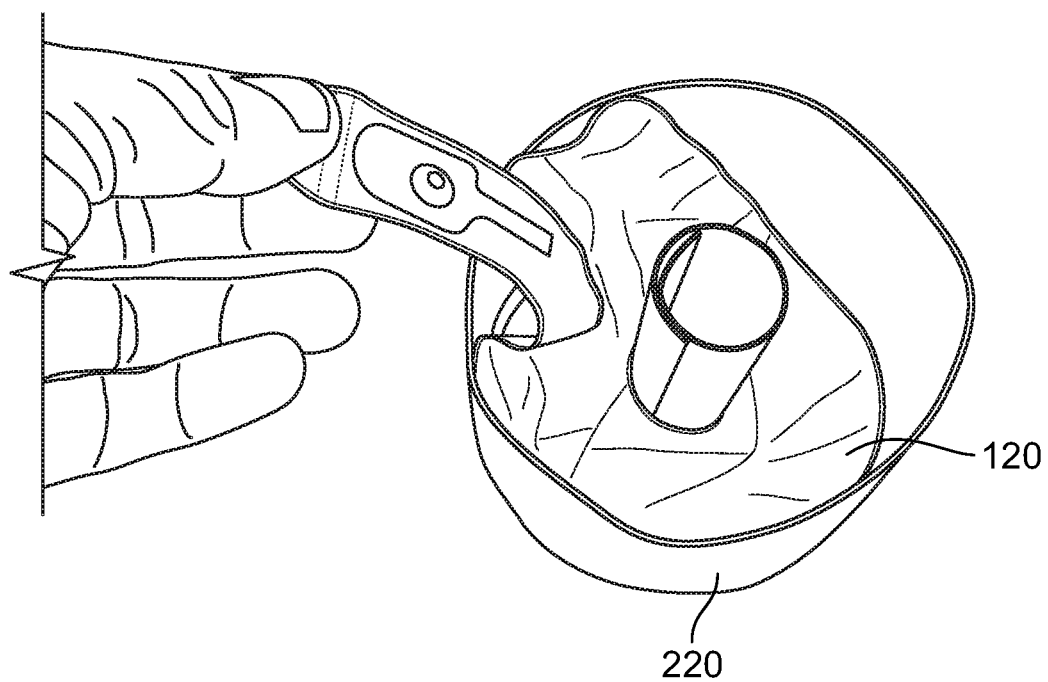
FIG. 25 show yet another approach for storing a container assembly.

In another approach (FIGS. 12-14), the container assembly 120 can include an integrated valve that uses an opposite side of container material 121 as flapper valve structure to thereby define a sealed or sealable container. Here, a port 140 can be sized and shaped to mate with an opening to the flex conduit or tube. The port 140 can be affixed such as by a glue joint 141 to an outside portion of the container sheet material 121. A movable support 144 including a foam assist member 146 can be provided on an opposite outside surface of the container sheet material 121. Under vacuum, the foam assist member 146 presses the sheet material 121 against the port 140 and a seal results. When there is positive pressure from the pump system which exceeds the forces provided by the foam assist member 146, then flow into the container can begin (FIG. 13). In one approach (FIG. 14), the support structure 144 can be attached to a hinge 148 and can further include a latch 150 for maintaining the support 144 in place against the container assembly. This approach lends itself to a very simple container assembly design. It is also contemplated that various parts of the valve can be disposable. The foam assist member 146 can be replaced as necessary when worn out, or should a seal be lost. Valve opening pressure can be adjusted by alternating foam density, increasing interference force provided by the movable support, or by changing the size of the foam assist member 146.

Installation of a container assembly with the port 140 is a simple process. The port 140 is pressed onto the pump outlet, and the support structure 144 is rotated into place. A latch 150 associated with the support 144 can be placed on securing structure to hold the support 144 in place.

Turning now to FIGS. 15-18, there are shown yet other approaches to valves for a container assembly. In a first approach (FIGS. 15-16), a standalone valve 160 with a silicone flapper 162 is contemplated. The valve 160 has a fill port 164 that can be attached to an outlet port of a pump system. In one particular embodiment, the flapper 162 can be cut from a 0.032 inch silicone sheet and have a long dimension on the order of 0.563 inches. Such dimensions and material can provide the flapper 162 with desired rigidity and flexibility to cooperate with the pump assembly to both allow milk flow into a container assembly and to prohibit milk escaping the container. A mounting surface 165 is provided on an underside of the valve, and the valve further includes a recess 166 against which the flapper 162 engages to seal the valve against egress and ingress.

In a related approach (FIGS. 17-18), there is provided a container assembly 120 with an integrated flapper valve 170 that facilitates defining a sealed or sealable container. A fill port 172 is provided and includes a mating and mounting face 174. The mating and mounting face 174 can be affixed to container material 121. A flapper 176 can be cut into the container material 121, the flapper 176 being sized and shaped to engage the mating and mounting face 174. Notably, the fill port 172 is affixed to an outer surface of the container material 121 over an incomplete circular cut (i.e., 300 degree cut) that forms the flapper 176.

In one or more approaches (FIG. 19), the container assembly can further or alternatively include a pulltab 180 affixed to valve structure 182. Here, the valve structure configured within an inlet port 183 can be removed by pulling on the pull tab 180. Accordingly, once the container assembly is full or it is no longer being used to receive milk, the valve structure 182 can be removed from the container assembly and milk can be poured out from the container through the inlet port 183.

As shown in FIG. 20, the container assembly can additionally or alternatively include integrated structure for facilitating maintaining an engagement with a pump system. In one contemplated approach, a hook or other latching structure 186 can be attached to the container assembly 120. The latching structure 186 can be rotatable or articulated to engage the pump system or an outlet tube 187 thereof to maintain a sealing engagement.

Turning now to FIG. 21, there is shown a container assembly 120 with an integrated bicuspid valve assembly 190 which facilitates defining a sealed or sealable container. A pair of 1.5 mil leaflets define the valve assembly 190 and are formed by attaching the leaflet material at one end, and bending the leaflet material approximately 180 degrees to thereby provided desired biasing. A machined flange defines an opening 192 to the container assembly 120 and seals (such as band seals) are employed to attach the material sheets comprising the assembly.

In yet another approach (FIG. 22), the container assembly 120 can be provided with a dispensing port 198 that provides structure for quick and easy transfer of milk from a container assembly to a bottle or other storage container. A seal configured at the dispensing port can be a ziplock arrangement, a peelable adhesive strip or a bar-seal that peels apart.

Figure 26:
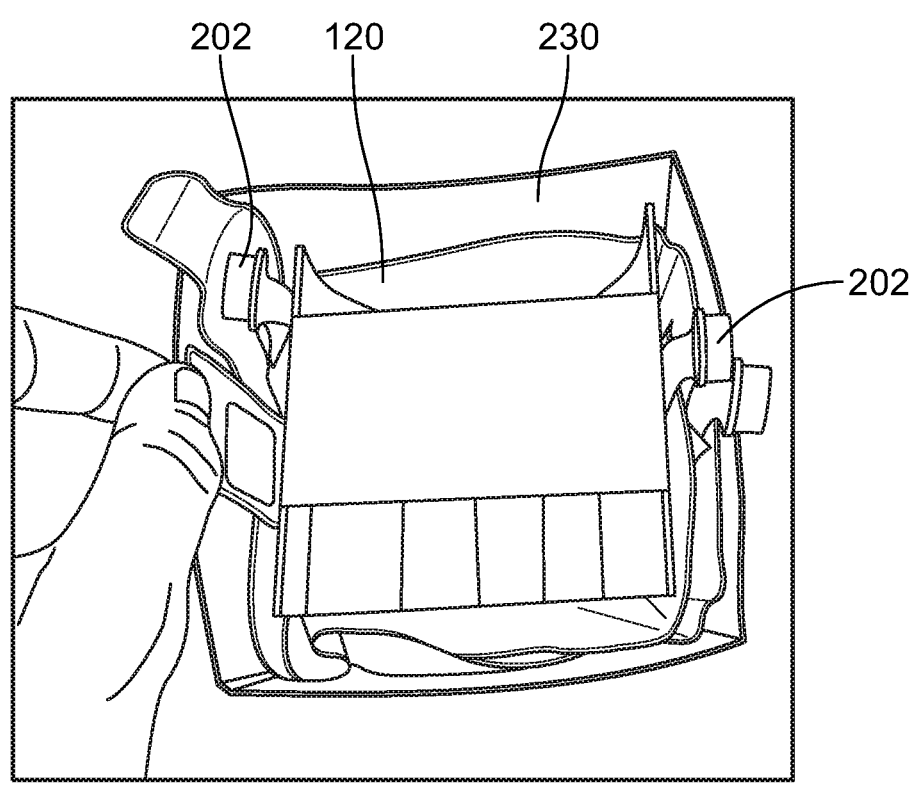
FIG. 26 shows a still further approach to storing and dispensing a container assembly.
Figure 27:
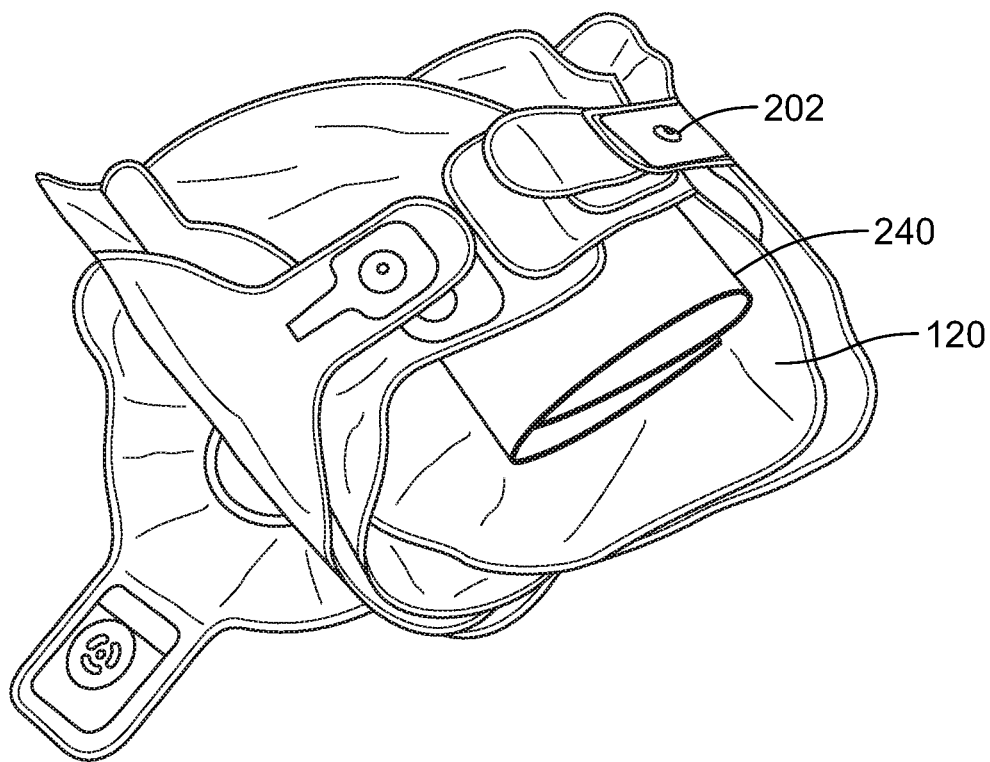
FIG. 27 shows structure for packaging container assemblies.
Figure 28A:
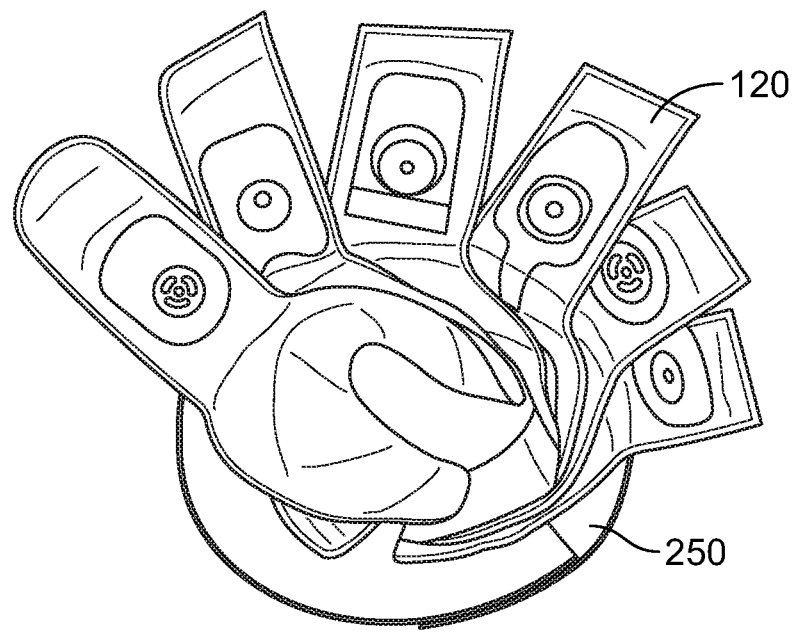
FIGS. 28A-B show alternative structure for packaging container assemblies.
Figure 28B:
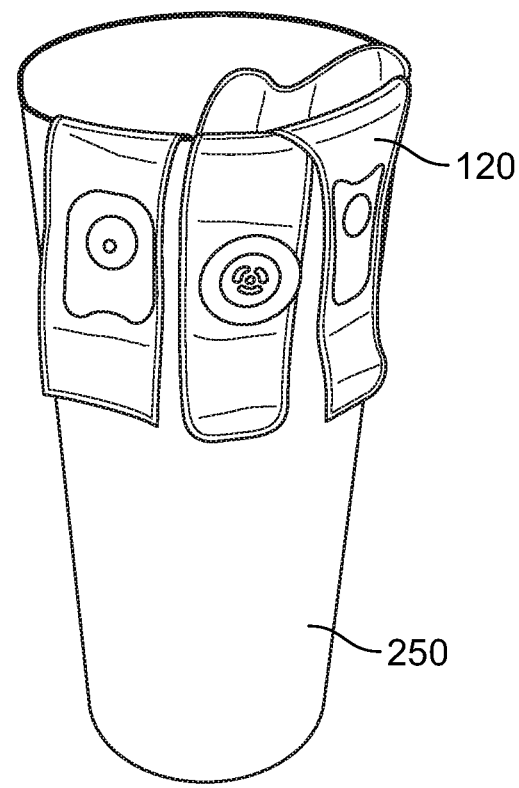
Figure 29:
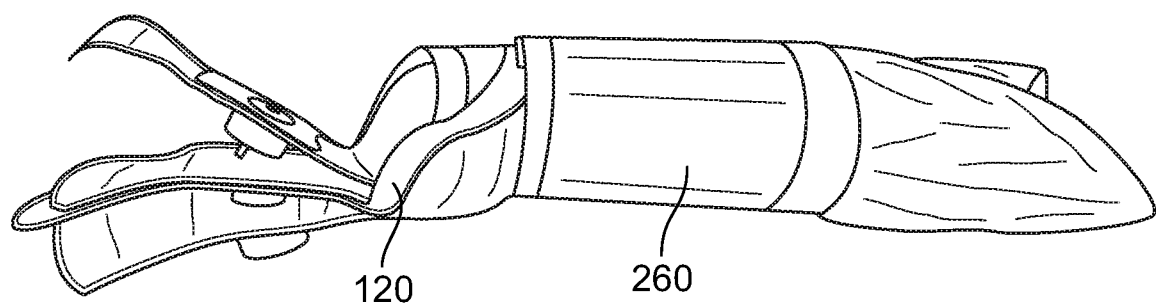
FIG. 29 shows yet another alternative approach for packaging container assemblies.

Referring to FIGS. 23-29, there are shown various approaches to packaging and storing container assemblies prior to use. The container can be pre-formed to optimize or maximize space within a pump system. Further, the container can be placed into a flattened configuration by applying a vacuum to facilitate effective packaging. In one approach (FIG. 23), container assemblies 120 can be laid flat in a stack in a generally rectangular receptacle 200. The valves 202 or other fitments forming inlets/outlets of the container assemblies 120 can be aligned or staggered within the receptacle 200. The receptacle 200 can further include a lid (not shown) which can be removed to gain access to the container assemblies 120, and the container assemblies can be removed as needed. In a second approach (FIG. 24), a receptacle 210 can further include a central column 212 sized and shaped to be received within a central opening formed in the container assemblies. The column 212 can assist in retaining the container assemblies 120 in an organized manner within the receptacle 210. In a related approach (FIG. 25), a generally cylindrical receptacle 220 can be equipped with a central column configured to assist in retaining container assemblies in a staggered fashion. In this specific approach, the container assemblies are folded into a depth of the receptacle 220. It is also contemplated that a receptacle can be defined by a generally square column 230 as shown in FIG. 26. Here, the valves or fitments 202 forming part of the container assemblies 120 can be configured on opposite sides of the receptacle 230 so that a more compact packaging arrangement can be presented.

In yet a further approach (FIG. 27), container assemblies 120 can be wrapped about an external surface of a tubular retaining body 240. The valves/fitments 202 of the container assemblies 120 can be conveniently grasped and the container assemblies 120 removed from the packaging as needed. Alternatively (FIG. 28), the container assemblies 120 can be stored within a tubular receptacle body 250 with the valves/fitments 202 of the container assemblies 120 being folded against the outside of the body 250. Additionally, the container assemblies 120 can simply be aligned and rolled into a bundle and held in place with a securing means for shipment.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the present disclosure.

That which is claimed is:

1. A container assembly for a pump, comprising:
   a body;
   a neck portion; and
   a valve assembly;
   wherein the valve assembly is configured to mate with the pump and the container assembly defines a sealed or sealable structure in combination with the pump and the valve assembly further includes an integrated valve, the integrated valve including a port formed on a first outside surface of the container assembly and a foam assist member configured on an opposite outside surface of the container assembly, the foam assist member maintaining the port closed until an opening pressure is reached.

2. The container assembly of claim 1, wherein the valve assembly is integrated into the container assembly.

3. The container assembly of claim 1, wherein the container assembly is sealed.

4. The container assembly of claim 1, wherein the container assembly is airtight.

5. The container assembly of claim 1, wherein the container assembly is formed from two sheets of material band welded together along a perimeter.

6. The container assembly of claim 1, wherein the valve permits milk inflow into the container assembly but prevents backflow.

7. The container assembly of claim 1, further comprising an hole formed in the neck portion and a grommet attached to the neck, wherein the grommet provides support to the container assembly when the container assembly is attached to an outlet of the pump.

8. The container assembly of claim 1, wherein the valve opens to allow flow into the container assembly at about 25 mm Hg.

9. The container assembly of claim 1, further comprising a support attached to the foam assist member, a hinge attached to the support that permits the support to rotate, and a latch for retaining the support in a position for engaging the foam assist member with the container assembly.

10. The container assembly of claim 1, wherein the valve assembly includes a flapper.

11. The container assembly of claim 1, wherein a portion of the neck includes a punched out portion, the punched out portion cooperating with a port to define an integrated valve.

12. The container assembly of claim 1, further comprising a pull tab connected to the valve assembly, wherein pulling on a pull tab results in removing the valve from the container assembly.

13. The container assembly of claim 1, further comprising a latch which can be rotated into engagement with the pump.

14. The container assembly of claim 1, wherein the valve is a bicuspid valve formed by a pair of leaflets contained within an interior of the neck portion.

15. The container of claim 1, further comprising a outlet formed by the body of the container assembly, the outlet created by separating sheets forming the body of the container assembly.

* * * * *